United States Patent [19]

Cadell et al.

[11] Patent Number: 4,958,645

[45] Date of Patent: Sep. 25, 1990

[54] MULTI-CHANNEL DIGITAL MEDICAL TELEMETRY SYSTEM

[75] Inventors: Theodore E. Cadell, Waterloo; Kevin Rabalais, Kitchener, both of Canada

[73] Assignee: CME Telemetrix Inc., Waterloo, Canada

[21] Appl. No.: 271,637

[22] Filed: Nov. 16, 1988

[30] Foreign Application Priority Data

Nov. 18, 1987 [GB] United Kingdom ............... 8726933

[51] Int. Cl.$^5$ ..................... H04B 1/00; G08C 17/00
[52] U.S. Cl. .................................. 128/903
[58] Field of Search ................ 128/903, 696, 363, 709

[56] References Cited

U.S. PATENT DOCUMENTS

| | | | |
|---|---|---|---|
| 3,087,117 | 4/1963 | Mitchell | 128/903 |
| 3,572,316 | 3/1971 | Vogelman et al. | 128/903 |
| 3,646,606 | 2/1972 | Buxton et al. | 128/903 |
| 3,815,109 | 6/1974 | Carraway et al. | 128/903 |
| 3,972,320 | 8/1976 | Kalman | 128/706 |
| 4,194,179 | 3/1980 | Malinouskas | 128/903 |
| 4,281,664 | 8/1981 | Duggan | 128/903 |
| 4,326,289 | 4/1982 | Dickinson | 455/2 |
| 4,566,133 | 1/1986 | Rambo | 455/65 |
| 4,593,273 | 6/1986 | Narcisse | 128/903 |
| 4,675,656 | 6/1987 | Narcisse | 128/903 |
| 4,791,933 | 12/1988 | Asai et al. | 128/696 |
| 4,819,860 | 4/1989 | Hargrove et al. | 128/903 |
| 4,827,943 | 5/1989 | Bornn et al. | 128/903 |
| 4,854,328 | 8/1989 | Pollack | 128/903 |

OTHER PUBLICATIONS

Fell et al., "A Four-Channel Ultrasonic Telemetry System for Obtaining Physiological Data . . .," Biotelemetry No. 1, 50–59, 1974.

Groeneveld, "Infra-red Controlled Command Receiver for Implantable Telemetry," Med. & Biol. Eng. & Comput., 1983, 21, 227–228.

Klien et al., "Development and Adjustment of a Multi-Channel . . . Telemetering System . . .," Int. Symp. on Biotelemetry, Nijmegen Neth. (5–1971).

Pauley et al., "A Microminiature Hybrid Multichannel Implantable Biotelemetry System," Biotelemetry Patient Monitg. 8: No. 3, 163–172, 1981.

Marko, "Multi-Channel Personal Telemetry System Using PPM," Aerospace Medicine, vol. 32, pp. 1019–1022, 1961.

Primary Examiner—Kyle L. Howell
Assistant Examiner—Kennedy J. Schaetzle
Attorney, Agent, or Firm—Daryl W. Schnurr

[57] ABSTRACT

A medical radio telemetry system has a plurality of telemeters with one telemeter being located on each patient. Each telemeter is connected to the patient to collect data such as temperature, heart rate, pacer rate, respiration rate, brain activity level and blood pressure level. Each telemeter has a patient locator system that functions in conjunction with one or more room locator transmitters. The room locator transmitters are spaced in the rooms or area where the location of a patient is being monitored. A signal from the patient locator transmitter is passed to the patient telemeter. All signals received by the patient telemeter are transmitted to an antenna system that is connected to a receiver. Preferably, there is more than one antenna system with means for switching between the systems to obtain the best signal. Each telemeter has up to six channels so that six separate signals can be sent to the receiver simultaneously. The receiver is connected to a display means for the signals.

11 Claims, 5 Drawing Sheets

MULTI-CHANNEL DIGITAL MEDICAL TELEMETRY SYSTEM

BACKGROUND OF THE INVENTION

1. Field of the Invention

This invention relates to a medical multi-channel radio telemetry system for remotely monitoring patients in a hospital.

2. Description of the Prior Art

Bedside (wired) and ambulatory (wireless) telemetry systems have been used for many years to monitor the performance of the heart and other vital signs of post-coronary and other at-risk patients. While the bedside monitors have been connected to a number of electrodes to monitor various parameters, ambulatory systems have been mostly single channel due to the limitations of the FM-FM carrier system used.

Existing ambulatory systems are able to provide one signal only showing such features as temperature only, heart rate only, or the shape of the heart pulse only, but give no indication of the location of the patient. Bedside systems are traditionally connected back to the central station by means of co-ax or multi-wire cables and are thus difficult to relocate or revise.

Many existing telemetry systems operating in a hospital produce signals that are subject to multi-path cancellations at the receiving antenna and thus "dead-spots" where little or no signal is present. One method employed to overcome this problem is to use active antennas which incorporate a built-in amplifier or to use a large number of antennas placed very close to one another. Unfortunately, this method often increases the number of, or level of, signal attenuations experienced in the dead spots.

The technology of existing systems is based on analog FM-FM transmission where the analog signal being monitored is used to frequency modulate an RF carrier. Such a system, by the nature of the demodulation process, requires a signal-to-noise ratio at the receiver of at least 10db to give a useable signal. Since the output power of the transmitter is limited (due to Federal Communications Commission regulations designed to prevent interference to other users) this signal-to-noise ratio requirement limits the useful range of the signal and sets limits on the ability of such a system to work in electrically noisy hospital environments.

SUMMARY OF THE INVENTION

It is an object of the present invention to provide a medical radio telemetry system having at least two channels where signals received from a patient are converted to digital signals for transmission to a receiver where the signals may be reconverted to analog signals or handled directly by computer.

A medical radio telemetry system for remotely monitoring patients in accordance with the present invention has a plurality of patient telemeters. Each telemeter is adapted to be mounted on a patient and has a transmitter and data collection means, said transmitter being connected to said data collection means to obtain data from said patient. Each transmitter has a transmitting antenna system. The data collection means includes receiving means to receive signals from a room locator transmitter, said data collection means obtaining any analog signals from the patient. There are means to convert any analog signals obtained from the patient to digital signals for transmission via said transmitting antenna system. Each transmitter has at least two channels. The telemetry system has a receiving antenna system, a receiver and display means, said receiving antenna system being capable of receiving signals from the transmitters of the telemeters and is connected to transfer said signals to said receiver. The receiver is connected to means for converting said signals from digital signals to analog signals, if desired, for transfer to said display means. The transmitters, room locator transmitter, receiver, receiving means and the transmitting and receiving antenna systems each having a power source.

BRIEF DESCRIPTION OF THE DRAWINGS

In drawings which illustrate a preferred embodiment of the invention.

DESCRIPTION OF A PREFERRED EMBODIMENT

Figure 1:
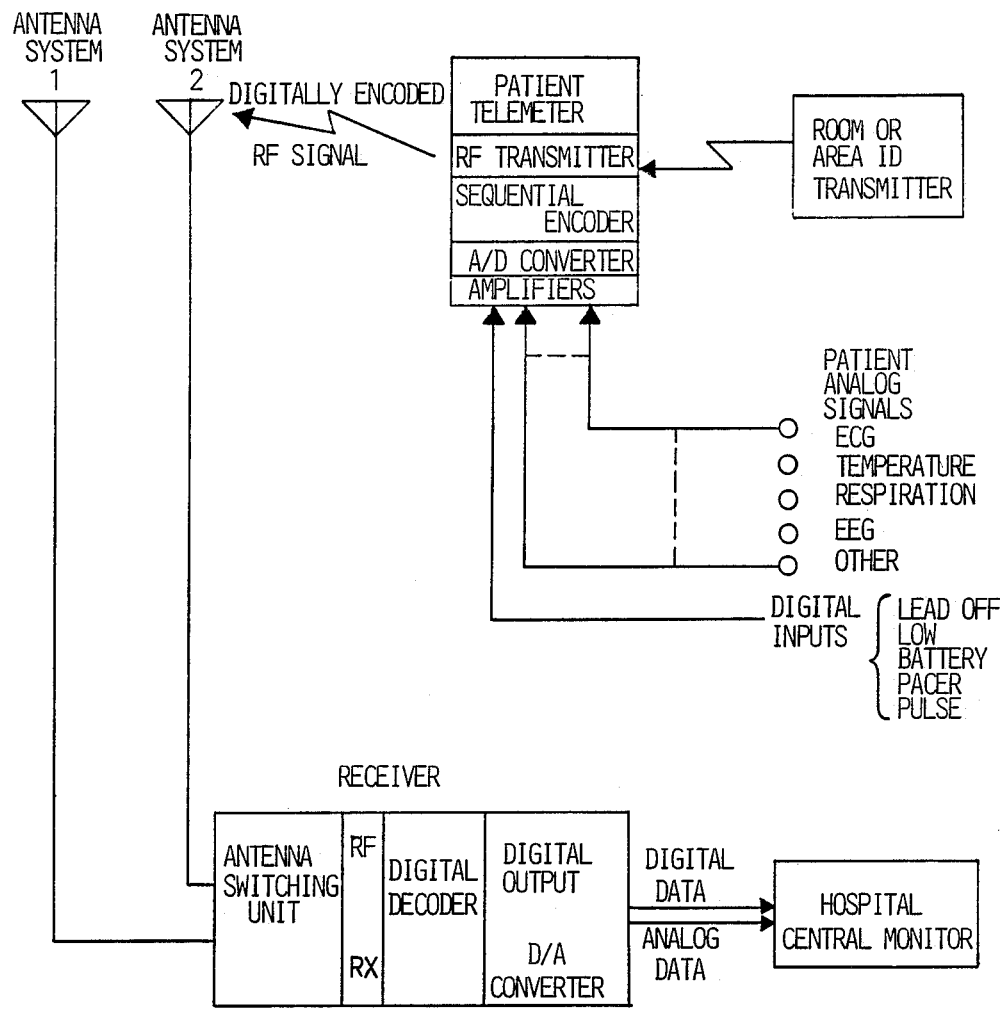
FIG. 1 is a block diagram of one embodiment of a telemetry system.

Referring to FIG. 1 in greater detail, it can be seen that a patient telemeter mounted on a patient is connected to receive signals from the patient in analog form. These signals can include one or more of temperature, heart rate, shape of heart pulse, pacer rate, patient locator signal, respiration rate, brain activity and blood pressure. Of course, other signals could be taken from the patient as well. These signals are received from the patient in analog form and converted by means located within the patient telemeter into digital signals. In addition, the patient telemeter contains receiving means for receiving signals from a room locator transmitter. There are a plurality of room locator transmitters located throughout the area where a patient might be located. The room locator transmitters each emit a distinct signal. The receiving means in the patient telemeter can receive a signal from any of the room locator transmitters and the patient telemeter can transmit that signal in digital together with all of the other signals received from the patient to a transmitting antenna system located on the telemeter. The transmitting antenna system transmits the signal or signals to a receiving antenna system which is connected to a receiver.

As shown in FIG. 1, the telemetry system preferably has at least two separate receiving antenna systems. Each receiving antenna system is connected to an antenna switching unit and to a receiver. The antenna switching unit activates either one of the receiving antenna systems. The receiver then receives a signal or signals from the activated receiving antenna system and either converts those signals to analog signals and transmits them to display means such as a central monitor or transmits all or some of said signals in digital form directly to the display means. The room or area transmitters, patient telemeter, receiving antenna systems, receiver and display means all have a power source (not shown). The telemetry system is a multi-channel system where the number of analog input channels ranges from two to six. Additional digital encoding channels are utilized to receive and transmit a signal for locating a patient.

Figure 2:
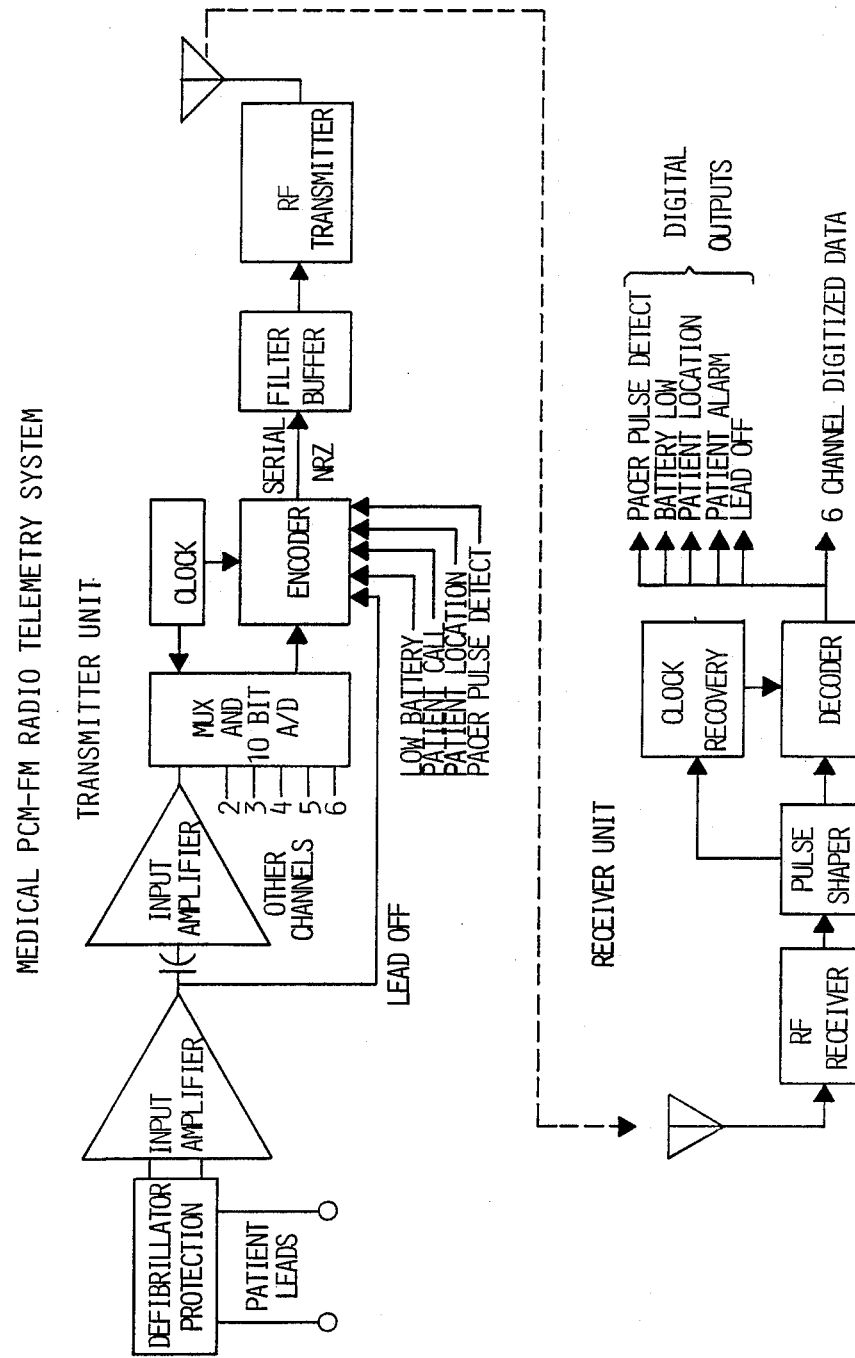
FIG. 2 is a block diagram of a transmitter and receiver for the system of FIG. 1.

In FIG. 2, a patient telemeter and receiver are shown in more detail. Patient electrodes are connected to the patient. The electrodes are conventional and transmit signals from the patient through a defibrillator protector and to an input amplifier. The electrodes can be designed to function as the transmitting antenna system for the telemeter. The signals are then passed to an A/D converter for conversion from analog to digital form. From the converter, the signals are passed to an encoder for digitally encoding in a serial format at an optimal bit rate. This digitally coded signal is then used to pulse modulate a VHF-FM carrier which is transmitted through the antenna system to the receiver. At the receiver, the RF signal is amplified, processed by the pulse shaper, demodulated, decoded and the digital signal is used directly on a display means or is converted back to analog for viewing on an analog display.

The telemetry system of the present invention is more immune to interfering electrical noise than prior art systems. In addition, the system provides inherent advantages in that it is able to handle digital inputs directly without conversion and is able to analyze digital output directly for error detection. The digital output can also be used for direct connection to computers and for signal processing in a digital format.

The transmitter in the patient telemeter converts the analog EKG into digital format and modulates this information onto a VHF carrier. In the particular model shown in FIG. 2, there are three different diagnostic quality EKG channels, a patient call button, pacer pulse detection and the inputs are protected against defibrillator shock. The unit is powered by a single 9-volt battery. All channels have differential input: Channel 1 uses three electrodes—two electrodes for different EKG inputs and the third electrode for a reference ground. Channels 3 to 6 use two electrodes each for each of the remaining signal inputs. The receiver extracts the digital information which is in turn converted back to analog and passed onto the display means.

Figure 3:
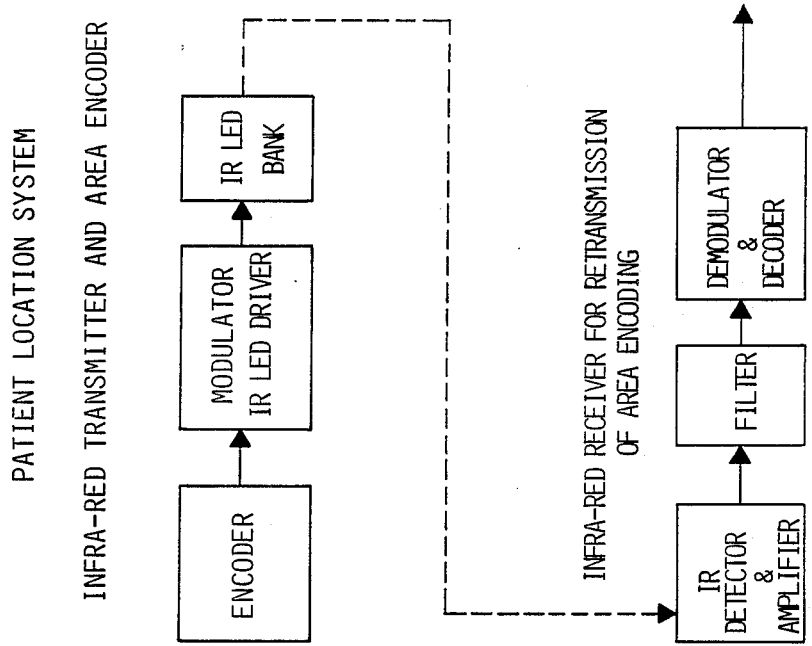
FIG. 3 is a block diagram of part of a patient locator system having coated light emitting diodes and a receiver for use in conjunction with a transmitter mounted on a patient.

Referring to FIG. 3, the patient locator system has a plurality of room locator transmitters located throughout an area where a patient might be located. Each room locator transmitter emits a distinct signal. The transmitter IR LED BANK outputs infra-red light modulated by the encoding signal. The patient telemeter contains receiving means to receive signals from the infra-red light emitting diode bank. In a preferred embodiment, this receiving means is a PIN photo diode. These signals are filtered, amplified and decoded so that the location of the particular infra-red transmitter signal received is passed onto the encoder in the patient telemeter for ultimate transmission to the display means. While infra-red light is preferred, the patient locator system could be designed to operate by transmitting ultrasound signals.

Figure 4:
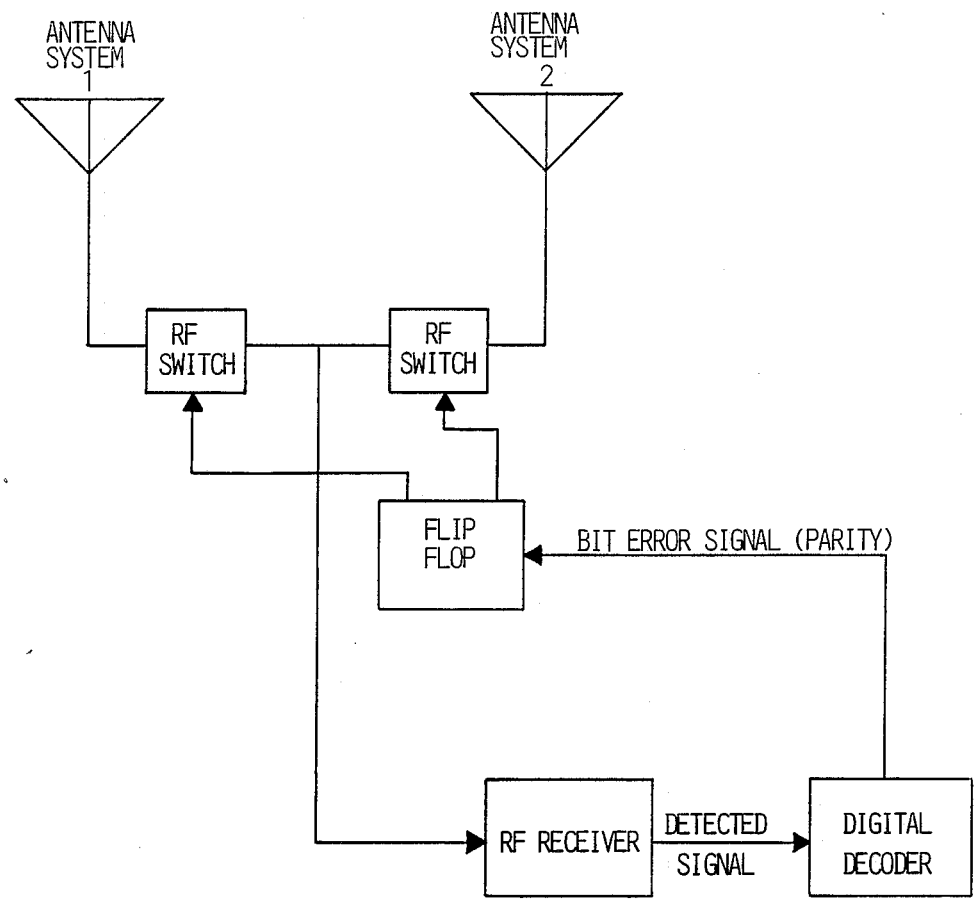
FIG. 4 is a block diagram of two antenna systems with means from switching from one system to another.
Figure 5:
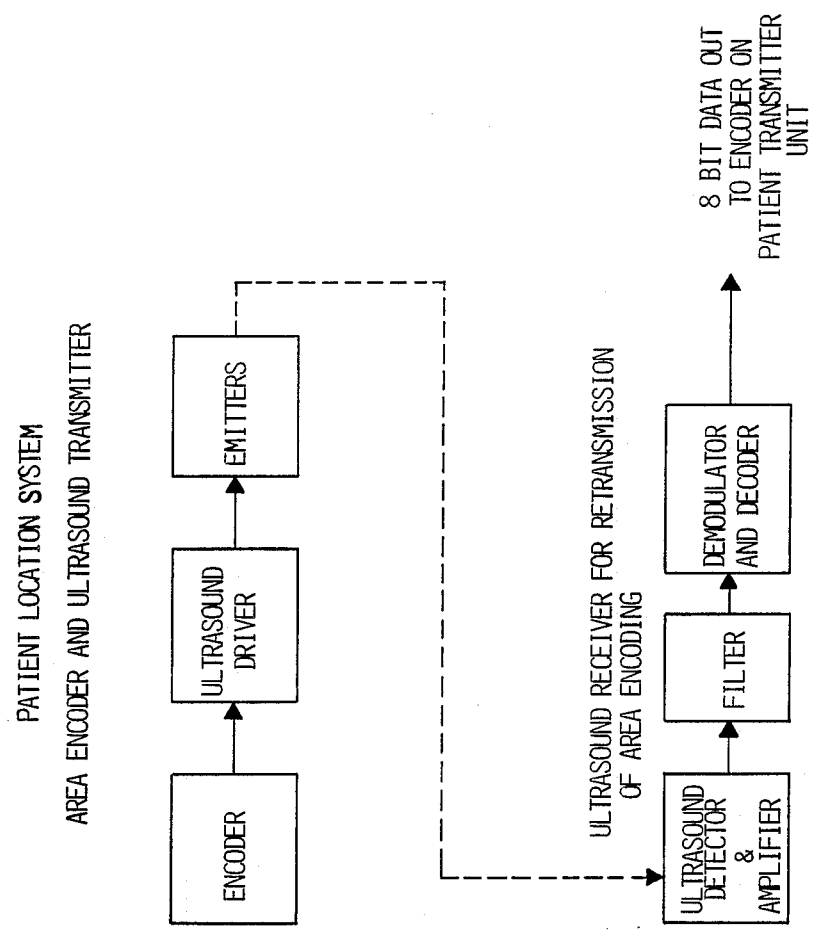

In FIG. 4, there is shown two antenna systems, each system having an RF switch, the RF switches being controlled by a flip-flop switch. Preferably, two or more independent antenna systems are spaced irregularly throughout an area where a patient might be monitored. When a digital error or bit error is detected, the flip-flop switch, which drives the RF switches, automatically switches from one antenna system to the other so that the receiver receives the best signal available and passes this signal onto the digital decoder. Preferably, the system is designed so that the flip-flop switch is programmed to latch onto the signal with the lowest errors and to periodically check for a better signal on another antenna system. The means to switch from one system to another can be programmed to switch when a parity bit error is detected.

In Table 1, there is set out an example of a typical specification for a telemetry system of the present invention. The minimum and maximum described in the specification are suggested limits for one particular system only and the present invention is not limited in any way by the specification.

TABLE 1

MEDICAL TELEMETRY SYSTEM SAMPLE SPECIFICATION

|  | Min. | Typical | Max. | Units |
|---|---|---|---|---|
| Transmitter | | | | |
| RF Field Strength |  | 150 |  | $\mu V/m$ @ 30 m |
| Frequency Range |  |  | 216 | MHz |
| Modulation Type |  | Pulse Code Modulation - FM | | |
| Battery Life |  | 140 Hours based on use of a 9 volt Mercury cell 146X or equivalent | | |
| Amplifier Type |  | Differential Input | | |
| Input Impedance |  | 1.5 |  | M Ohms |
| Dynamic Range |  | ±5 |  | mv |
| Noise (RTI) |  | 5 |  | $\mu V$ p-p |
| Number of Analog Input Channels | 1 |  | 6 | Channels |
| Bandwidth | DC |  | 100 | Hz |
| Sample Rate |  |  | 1170 | Samples/sec |
| No. of Bits Encoding |  |  | 10 | Bits |
| Transmission Error Detection* |  | 4 |  | Bits |
| Digital Data Encoding |  | 20 |  | Bits |
| Size of Case |  | 10 × 15 × 3 |  | cm |
| Receiver | | | | |
| Sensitivity |  | 1 |  | $\mu V$ |
| Frequency Range | 174 |  | 216 | MHz |
| Overall Gain of System | 455 |  | 5000 | mV/mV |
| Size of Plug-in PCB |  | 26 × 12 |  | cm |
| Antenna System | | | | |
| Spatial Diversity | | | | |
| Controls | | | | |
| DC Offset: ± 2.0 V Minimum | | | | |
| Gain Control: X 455 to X 5000* | | | | |

TABLE 1-continued
MEDICAL TELEMETRY SYSTEM
SAMPLE SPECIFICATION

|  | Min. | Typical | Max. | Units |
|---|---|---|---|---|

Power ON/OFF
<u>Displays</u>
Power ON
<u>Output</u>
Parallel Pulse Coded Data + Channel No. + Data valid + Error Detect (16 bits)
Analog Output - One to six Channels
Digital Outputs for Battery Low, Lead Disconnect, Patient Alarm, Patient Location, and Digital Error Detect
<u>Options</u>
IR Control for Input Channel Select

*Error correction algorithms are also possible.

What we claim as our invention is:

1. A medical radio telemetry system for remotely monitoring patients, said system comprising a plurality of patient telemeters, each telemeter adapted to be mounted on a patient and having a transmitter and data collection means for obtaining patient data said transmitter being connected to said data collection means each transmitter having a transmitting antenna system, room locator means for producing signals indicative of patient location, said data collection means including receiving means to receive said signals from the room locator transmitter means, said data collection means obtaining analog signals from the patient said collection means including means for converting said analog signals to digital signals for transmission via said transmitting antenna system, each transmitter having at least two channels, said medical telemetry system having a receiving antenna system, a receiver and display means, said receiving antenna system being capable of receiving signals from the transmitters of the telemeters and being connected to transfer said digital signals to said receiver, said receiver being connected to means for converting said signals from digital signals to analog signals, if desired, for transfer to the display means, the transmitter, receiver and the transmitting and receiving antenna systems each having a power source.

2. A system as claimed in claim 1 wherein there are at least two receiving antenna systems with means for automatically switching from one receiving antenna system to the other in order to obtain the best signal.

3. A system as claimed in claim 2 wherein the number of channels ranges from two to six.

4. A system as claimed in claim 3 wherein the transmitter is connected to receive two to six signals from a patient, one signal for each channel, said signals being selected from the following group:
   (a) temperature;
   (b) heart rate;
   (c) shape of heart pulse;
   (d) pacer rate;
   (e) patient locator signal;
   (f) respiration rate;
   (g) battery level;
   (h) patient call;
   (i) brain activity; and
   (j) blood pressure.

5. A system as claimed in claim 4 wherein there are a plurality of room locator transmitter means located throughout an area where the patient might be located, each room locator transmitter means emitting a distinct signal, said receiving means of each patient telemeter being capable of receiving said signal from any of the room locator transmitter means, the patient telemeter transmitting said signals to the receiver.

6. A system as claimed in claim 5 wherein the room locator transmitter means are ultrasound transmitters.

7. A system as claimed in claim 4 wherein there are a plurality of coded light emitting diodes located throughout an area where the patient might be located, each light emitting diode emitting a distinct signal, the patient telemeter having receiving means to receive a signal from any of the light emitting diodes, the transmitter mounted on the patient transmitting said signal to the receiver.

8. A system as claimed in claim 7 wherein the receiving means in the patient telemeter has means to detect and decode infra-red location information received from a particular light emitting diode.

9. A system as claimed in claim 2 wherein there are more than two receiving antenna systems spaced irregularly throughout an area where the patient might be located and the means to switch from one system to another being a series of RF switches, one switch for each antenna system, switching occurring when a bit error is detected.

10. A system as claimed in claim 9 wherein the means to switch from one system to another is programmed to switch when a parity bit error is detected.

11. A system as claimed in claim 9 wherein a flip-flop switch drives the RF switches, the flip-flop switch being programmed to latch onto the signal with the lowest errors and to periodically check for a better signal on another antenna system.

* * * * *